United States Patent [19]

Chu

[11] Patent Number: 4,548,914

[45] Date of Patent: Oct. 22, 1985

[54] ZEOLITE CATALYSTS OF IMPROVED ACTIVITY AND PARA-SELECTIVITY

[75] Inventor: Chin-Chiun Chu, North Brunswick, N.J.

[73] Assignee: Mobil Oil Corporation, New York, N.Y.

[21] Appl. No.: 709,821

[22] Filed: Mar. 4, 1985

Related U.S. Application Data

[63] Continuation of Ser. No. 526,846, Aug. 26, 1983, abandoned, which is a continuation-in-part of Ser. No. 322,630, Nov. 19, 1981, abandoned.

[51] Int. Cl.$^4$ .............................................. B01J 29/28
[52] U.S. Cl. ...................................... 502/85; 502/77
[58] Field of Search .............................. 502/71, 77, 85

[56] References Cited

U.S. PATENT DOCUMENTS

| | | | |
|---|---|---|---|
| 3,972,832 | 8/1976 | Butter et al. | 502/77 |
| 4,137,195 | 1/1979 | Chu | 502/77 |
| 4,409,132 | 10/1983 | Forbus et al. | 502/77 |
| 4,420,418 | 12/1983 | Chu | 502/77 |

FOREIGN PATENT DOCUMENTS 0030796  6/1981  European Pat. Off. .

*Primary Examiner*—Carl F. Dees
*Attorney, Agent, or Firm*—Alexander J. McKillop; Michael G. Gilman; Edward F. Kenehan, Jr.

[57] ABSTRACT

A method is provided for treating modified ZSM-5 type zeolite catalysts with water vapor in order to enhance the aromatics conversion activity and/or the para-selective properties of such catalysts for the conversion of aromatic materials. The modified zeolites so treated are those which contain a minor proportion of a difficultly reducible oxide such as magnesium oxide, calcium oxide and/or phosphorus oxide. Such catalyst compositions can be used in alkylation, transalkylation or disproportionation processes to provide improved yields of alkylated aromatic product mixtures having exceptionally high concentrations of the para-dialkylbenzene isomer.

12 Claims, No Drawings

ZEOLITE CATALYSTS OF IMPROVED ACTIVITY AND PARA-SELECTIVITY

CROSS-REFERENCE TO RELATED APPLICATIONS

This is a continuation of copending application Ser. No. 526,846, filed on Aug. 26, 1983 now abandoned and which is a continuation-in-part of applicant's copending U.S. application Ser. No. 322,630, filed Nov. 19, 1981, now abandoned. This application is also related to applicant's copending U.S. application Ser. No. 322,629, filed Nov. 19, 1981, now U.S. Pat. No. 4,420,418. The entire disclosures of these two above-cited applications are expressly incorporated herein by reference.

BACKGROUND OF THE INVENTION

1. Field of the Invention

The present invention relates to the preparation and use of modified zeolite catalyst compositions which are especially suitable for the conversion of aromatic hydrocarbons to provide product mixtures enriched in the para-(or 1,4-)dialkyl substituted benzene isomer.

2. Description of the Prior Art

Production of dialkyl substituted benzene compounds via alkylation, transalkylation or disproportionation of aromatic hydrocarbons is an important step in a number of commercial chemical manufacturing processes. Such reactions can be carried out over a variety of catalyst materials. Alkylation of aromatic hydrocarbons utilizing crystalline aluminosilicate catalysts has, for example, been described. U.S. Pat. No. 2,904,697 to Mattox refers to alkylation of aromatic hydrocarbons with an olefin in the presence of a crystalline metallic aluminosilicate having uniform openings of about 6 to 15 Angstrom units. U.S. Pat. No. 3,251,897 to Wise describes alkylation of aromatic hydrocarbons in the presence of X or Y-type crystalline aluminosilicate zeolites, specifically such type zeolites wherein the cation is rare earth and/or hydrogen. U.S. Pat. No. 3,751,504 to Keown et al. and U.S. Pat. No. 3,751,506 to Burress describe vapor phase alkylation of aromatic hydrocarbons with olefins, e.g., benzene with ethylene, in the presence of a ZSM-5 type zeolite catalyst.

The disproportionation of aromatic hydrocarbons in the presence of zeolite catalysts has been described by Grandio et al in the *Oil and Gas Journal*, Vol. 69, No. 48 (1971), U.S. Pat. Nos. 3,126,422; 3,413,374, 3,598,878; 3,598,879 and 3,607,961 show vapor-phase disproportionation of toluene over various catalysts.

In many of these prior art processes, the dialkylbenzene product produced frequently contains more of the 1,3 isomer than of the other two isomers. For example, xylene produced via the conventional catalytic methylation of toluene can have the equilibrium composition of approximately 24 percent of 1,4-, 54 percent of 1,3- and 22 percent of 1,2-isomer. Of the dialkylbenzene isomers, 1,3-dialkylbenzene is often the least desired product, with 1,2- and 1,4-dialkylbenzene being the more useful products. 1,4-Dimethylbenzene, for example, is of particular value, being useful in the manufacture of terephthalic acid which is an intermediate in the manufacture of synthetic fibers such as "Dacron". Furthermore, 1,4-methylethylbenzene, i.e., para-ethyltoluene (PET), is useful for subsequent conversion to para-methylstyrene, and for this purpose ethyltoluene products containing as much as 97% of the para isomer can be required.

Mixtures of dialkylbenzene isomers, either alone or in further admixture with ethylbenzene, have previously been separated by expensive superfractionation and multistage refrigeration steps. Such processes, as will be realized, involve high operation costs and hAve a limited yield. Alternatively, various modified zeolite catalysts have been developed to alkylate toluene with a greater or lesser degree of selectivity to 1,4-dialkylbenzene isomers. Hence, U.S. Pat. Nos. 3,972,832, 4,034,053, 4,128,592, and 4,137,195 disclose particular zeolite catalysts which have been treated with compounds of phosphorus and/or magnesium to increase para-selectivity of the catalysts. Para-selective boron-containing zeolites are shown in U.S. Pat. No. 4,067,920 and para-selective, antimony-containing zeolites in U.S. Pat. No. 3,979,472. Similarly, U.S. Pat. Nos. 3,965,208; 4,117,026; 4,259,537; 4,260,843; 4,275,256; 4,276,437; 4,276,438; 4,278,827 and 4,288,647 all disclose other zeolites modified with various oxides to improve catalyst para-selectivity.

European Patent Application Publication No. 30,796 describes a process for decreasing the para-selectivity of a zeolite catalyst by passing moist air over the catalyst at ambient temperature. The decrease in para-selectivity obtained by such a treatment may be in excess of 25%. More particularly, for example, para-selectivity decreases from 90% to 62% by such a treatment with moist air according to Example 1 of the European Patent Application Publication No. 30,796.

Notwithstanding the existence of such chemically-modified zeolite catalysts having para-selective properties, there is a continuing need to develop additional types of catalytic materials which are highly para-selective when used for the conversion of aromatic compounds to dialkyl benzene products. Accordingly, it is an object of the present invention to provide treated modified zeolite catalyst compositions which effectively promote the conversion of aromatics to produce mixtures containing an exceptionally high percentage, e.g., 80% by weight or more for alkylation of toluene, of para-dialkylbenzene isomer.

It is a further object of the present invention to provide methods of preparing such catalysts of improved activity and high para-selectivity.

It is a further object of the present invention to provide highly para-selective aromatics conversion processes employing the modified zeolite catalysts described herein.

SUMMARY OF THE INVENTION

The present invention relates to a method for treating modified zeolite catalysts to render such catalysts both active and highly para-selective for the conversion of aromatic compounds to produce dialkyl substituted benzene compounds. The zeolite component of the catalysts so treated is one which has a silica to alumina mole ratio of at least 12 and a constraint index within the approximate range of 1 to 12. Such zeolite catalysts are further modified by incorporation thereinto of a minor proportion of a difficulty reducible oxide.

In accordance with the present invention, an inert inorganic gaseous diluent is contacted with liquid water under conditions such that the diluent becomes essentially saturated with water in the vapor state, and whereby water in the liquid state becomes dispersed in the diluent, e.g., as a fine mist. The water content of the moistened diluent may exceed the gaseous water vapor saturation amount by, e.g., at least about 50%.

After the diluent is so moistened with water, the liquid water portion thereof is essentially all converted to gaseous water by heating the moistened diluent to a temperature sufficient to accomplish this conversion. By means of this heating, the vapor pressure of water in the diluent may be increased by a factor of at least 2. In other terms, the temperature of the diluent may be increased by at least 15° C. during this heating step. More particularly, for example, the vapor pressure of water in the moistened diluent may be about 24 mm of Hg at about 25° C., whereas this vapor pressure may be increased to about 55 mm of Hg by heating to a temperature of about 40° C.

The essentially liquid water free diluent is then passed over the modified zeolite catalyst at a temperature between about 40° C. and 700° C. to achieve enhanced catalyst activity and/or para-selectivity. Surprisingly, the para-selectivity of the catalysts is not substantially decreased even when the activity of the catalyst is increased. The decrease in para-selectivity, if any, is generally never greater than about 2%.

The present invention also relates to modified catalyst compositions treated in this manner and to alkylation, transalkylation and disproportionation processes utilizing such treated modified catalyst compositions.

DETAILED DESCRIPTION OF THE INVENTION

The catalysts which are treated in accordance with the method of the present invention are zeolite based catalysts which promote the conversion of aromatic compounds. One essential component of such catalysts is a particular type of crystalline zeolite material which exhibits unusual properties. Although these zeolites have unusually low alumina contents, i.e. high silica to alumina mole ratios, they are very active even when the silica to alumina mole ratio exceeds 30. Such activity is surprising, since catalytic activity is generally attributed to framework aluminum atoms and/or cations associated with these aluminum atoms. These zeolites retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity. These zeolites, used as catalysts, generally have low coke-forming activity and therefore are conducive to long times on stream between regenerations by burning carbonaceous deposits with oxygen-containing gas such as air.

An important characteristic of the crystal structure of this particular class of zeolites is that it provides a selective constrained access to and egress from the intracrystalline free space by virtue of having an effective pore size intermediate between the small pore Linde A and the large pore Linde X, i.e. the pore windows of the structure are of about a size such as would be provided by 10-membered rings of silicon atoms interconnected by oxygen atoms. It is to be understood, of course, that these rings are those formed by the regular disposition of the tetrahedra making up the anionic framework of the crystalline zeolite, the oxygen atoms themselves being bonded to the silicon or aluminum atoms at the centers of the tetrahedra. Briefly, the preferred type zeolites useful in this invention possess, in combination: a silica to alumina mole ratio of at least about 12; and a structure providing constrained access to the intracrystalline free space.

The silica to alumina mole ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina mole ratio of at least 12 are useful, it is preferred in some instances to use zeolites having substantially higher silica/alumina ratios, e.g. 70 and above or even 1600 and above. In addition, zeolites as otherwise characterized herein but which are substantially free of aluminum, that is zeolites having silica to alumina mole ratios of up to infinity, are found to be useful and even preferable in some instances. Such "high silica" or "highly siliceous" zeolites are intended to be included within this decription. Also to be included within this definition are substantially pure silica analogs of the useful zeolites described herein, that is to say those zeolites having no measurable amount of aluminum (silica to alumina mole ratio of infinity) but which otherwise embody the characteristics disclosed.

Members of this particular class of zeolites, after activation, acquire an intracrystalline sorption capacity for normal hexane which is greater than that for water, i.e. they exhibit "hydrophobic" properties. This hydrophobic character can be used to advantage in some applications.

The zeolites of the particular class useful herein have an effective pore size such as to freely sorb normal hexane. In addition, their structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the desired type. Windows of 10-membered rings are preferred, although in some instances excessive puckering of the rings or pore blockage may render these zeolites ineffective. Twelve-membered rings usually do not offer sufficient constraint to produce the advantageous conversions, although the puckered 12-ring structure of TMA offretite shows constraind access. Other 12-ring structures may exist which may be operative.

Rather than attempt to judge from crystal structure whether or not a zeolite possesses the necessary constrained access to molecules of larger cross-section than normal paraffins, a simple determination of the "Constraint Index" as herein defined may be made by passing continuously a mixture of an equal weight of normal hexane and 3-methylpentane over a sample of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 540° C. for at least 15 minutes. The zeolite is then flushed with helium and the temperature is adjusted between 290° C. and 510° C. to give an overall conversion of between 10% and 60%. The mixture of hydrocarbons is passed at 1 liquid hourly space velocity (i.e., 1 volume of liquid hydrocarbon per volume of zeolite per hour) over the zeolite with a helium dilution to give a helium to (total) hydrocarbon mole ratio of 4:1. After 20 minutes on stream, a sample of the effluent is taken and analyzed, most conveniently by gas chromatography, to determine the fraction remaining unchanged for each of the two hydrocarbons.

The "Constraint Index" is calculated as follows:

$$\text{Constraint Index} = \frac{\log_{10}(\text{fraction of hexane remaining})}{\log_{10}(\text{fraction of 3-methylpentane remaining})}$$

The Constraint Index approximates the ratio of the cracking rate constants for the two hydrocarbons. Zeolites suitable for the present invention are those having a Constraint Index of about 1 to 12. Constraint Index (CI) values for some typical materials are:

| Zeolite | C.I. |
| --- | --- |
| ZSM-5 | 8.3 |
| ZSM-11 | 8.7 |
| ZSM-12 | 2 |
| ZSM-23 | 9.1 |
| ZSM-35 | 4.5 |
| ZSM-38 | 2 |
| ZSM-48 | 3.4 |
| TMA Offretite | 3.7 |
| Clinoptilolite | 3.4 |
| Beta | 1.5 |
| H—Zeolon (mordenite) | 0.4 |
| REY | 0.4 |
| Amorphous Silica-Alumina | 0.6 |
| Erionite | 38 |

The above-described Constraint Index is an important and even critical definition of those zeolites which are useful in the instant invention. The very nature of this parameter and the recited technique by which it is determined, however, admit of the possibility that a given zeolite can be tested under somewhat different conditions and thereby exhibit different Constraint Indices. Constraint Index seems to vary somewhat with severity of operation (conversion) and the presence or absence of binders. Likewise, other variables such as crystal size of the zeolite, the presence of occluded contaminants, etc., may affect the constraint index. Therefore, it will be appreciated that it may be possible to select test conditions as to establish more than one value in the range of 1 to 12 for the Constraint Index of a particular zeolite. Such a zeolite exhibits the constrained access as herein defined and is to be regarded as having a Constraint Index in the range of 1 to 12. Also contemplated herein as having a Constraint Index in the range of 1 to 12 and therefore within the scope of the defined class of highly siliceous zeolites are those zeolites which, when tested under two or more sets of conditions within the above-specified ranges of temperature and conversion, produce a value of the Constraint Index slightly less than 1, e.g. 0.9, or somewhat greater than 12, e.g. 14 or 15, with at least one other value within the range of 1 to 12. Thus, it should be understood that the Constraint Index value as used herein is an inclusive rather than a exclusive value. That is, a crystalline zeolite when identified by any combination of conditions within the testing definition set forth herein as having a Constraint Index in the range of 1 to 12 is intended to be included in the instant novel zeolite definition whether or not the same identical zeolite, when tested under other of the definition conditions, may give a Constraint Index value outside of the range of 1 to 12.

The particular class of zeolites defined herein is exemplified by ZSM-5, ZSM-11, ZSM-12, ZSM-23, ZSM-35, ZSM-38, ZSM-48 and other similar materials.

ZSM-5 is described in greater detail in U.S. Pat. Nos. 3,702,886 and Re 29,948. The entire descriptions contained within those patents, particularly the X-ray diffraction pattern of therein disclosed ZSM-5, are incorporated herein by reference.

ZSM-11 is described in U.S. Pat. No. 3,709,979. That description, and in particular the X-ray diffraction pattern of said ZSM-11, is incorporated herein by reference.

ZSM-12 is described in U.S. Pat. No. 3,832,449. That description, and in particular the X-ray diffraction pattern disclosed therein, is incorporated herein by reference.

ZSM-23 is described in U.S. Pat. No. 4,076,842. The entire content thereof, particularly the specification of the X-ray diffraction pattern of the disclosed zeolite, is incorporated herein by reference.

ZSM-35 is described in U.S. Pat. No. 4,016,245. The description of that zeolite, and particularly the X-ray diffraction pattern thereof, is incorporated herein by reference.

ZSM-38 is more particularly described in U.S. Pat. No. 4,046,859. The description of that zeolite, and particularly the specified X-ray diffraction pattern thereof, is incorporated herein by reference.

ZSM-48 is more particularly described in U.S. Pat. No. 4,375,573 and in published European Patent Application No. 80 300,463, the entire content of which is incorporated herein by reference.

It is to be understood that by incorporating by reference the foregoing patents to describe examples of specific members of the specified zeolite class with greater particularity, it is intended that identification of the therein disclosed crystalline zeolites be resolved on the basis of their respective X-ray diffraction patterns. As discussed above, the present invention contemplates utilization of such catalyst wherein the mole ratio of silica to alumina is essentially unbounded. The incorporation of the identified patents should therefore not be construed as limiting the disclosed crystalline zeolites to those having the specific silica-alumina mole ratios discussed therein, it now being known that such zeolites may be substantially aluminum-free and yet, having the same crystal structure as the disclosed materials, may be useful or even preferred in some applications. It is the crystal structure, as identified by the X-ray diffraction "fingerprint", which establishes the identity of the specific crystalline zeolite material.

The specific zeolites described, when prepared in the presence of organic cations, are substantially catalytically inactive, possibly because the intra-crystalline free space is occupied by organic cations from the forming solution. They may be activated by heating in an inert atmosphere at 540° C. for one hour, for example, followed by base exchange with ammonium salts followed by calcination at 540° C. in air. The presence of organic cations in the forming solution may not be absolutely essential to the formation of this type zeolite; however, the presence of these cations does appear to favor the formation of this special class of zeolite. More generally, it is desirable to activate this type catalyst by base exchange with ammonium salts followed by calcination in air at about 540° C. for from about 15 minutes to about 24 hours.

Natural zeolites may sometimes be converted to zeolite structures of the class herein identified by various activation procedures and other treatments such as base exchange, steaming, alumina extraction and calcination, alone or in combinations. Natural minerals which may be so treated include ferrierite, brewsterite, stilbite, dachiardite, epistilbite, heulandite, and clinoptilolite.

The preferred crystalline zeolites for utilization herein include ZSM-5, ZSM-11, ZSM-12, ZSM-23, ZSM-35, ZSM-38 and ZSM-48, with ZSM-5 being particularly preferred.

In a preferred aspect of this invention, the zeolites hereof are selected as those provided among other things a crystal framework density, in the dry hydrogen form, of not less than about 1.6 grams per cubic centimeter. It has been found that zeolites which satisfy all three of the discussed criteria are most desired.

Therefore, the preferred zeolites useful with respect to this invention are those having a Constraint Index as defined above of about 1 to about 12, a silica to alumina mole ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on Page 19 of the article Zeolite Structure by W. M. Meier. This paper, the entire contents of which are incorporated herein by reference, is included in *Proceedings of the Conference on Molecular Sieves*, (London, April 1967) published by the Society of Chemical Industry, London, 1968.

When the crystal structure is unknown, the crystal framework density may be determined by classical pycnometer techniques. For example, it may be determined by immersing the dry hydrogen form of the zeolite in an organic solvent which is not sorbed by the crystal. Or, the crystal density may be determined by mercury porosimetry, since mercury will fill the interstices between crystals but will not penetrate the intracrystalline free space.

It is possible that the unusual sustained activity and stability of this special class of zeolites is associated with its high crystal anionic framework density of not less than about 1.6 grams per cubic centimeter. This high density must necessarily be associated with a relatively small amount of free space within the crystal, which might be expected to result in more stable structures. This free space, however, is important as the locus of catalytic activity.

Crystal framework densities of some typical zeolites, including some which are not within the purview of this invention, are:

|  | Void Volume | Framework Density |
|---|---|---|
| Ferrierite | 0.28 cc/cc | 1.76 g/cc |
| Mordenite | .28 | 1.7 |
| ZSM-5, -11 | .29 | 1.79 |
| ZSM-12 | — | 1.8 |
| ZSM-23 | — | 2.0 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight may be used as precursors to the alkaline-earth metal modified zeolites of the present invention. Thus, the original alkali metal of the zeolite may be replaced by ion exchange with other suitable metal cations of Groups I through VIII of the Periodic Table, including, by way of example, nickel, copper, zinc, palladium, calcium or rare earth metals.

In practicing aromatics conversion processes using the treated catalyst of the present invention, it may be useful to incorporate the above-described crystalline zeolites with a matrix comprising another material resistant to the temperature and other conditions employed in such processes. Such matrix materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constitutent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as alumina, silica-alumina, silica-magnesia, silica-zirconia, silica-thoria, silica-beryllia, and silica-titania, as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix, on an anhydrous basis, may vary widely with the zeolite content ranging from between about 1 to about 99 percent by weight and more usually in the range of about 5 to about 80 percent by weight of the dry composite.

A second essential component of the aromatics conversion catalysts treated in accordance with the present invention comprises a minor proportion, e.g., from about 0.05% to 50% by weight of the catalyst composite, of a difficultly reducible oxide. Oxides of this type can include oxides of phosphorus as well as those oxides of the metals of Groups IA, IIA, IIIA, IVA, VA, VIA, VIIA, VIIIA, IB, IIB, IIIB, IVB, or VB of the Periodic Chart of the Elements (Fisher Scientific Company, Catalog No. 5-702-10) which serve to enhance the para-selectivity properties of the catalysts modified there-with. The difficulty reducible oxides most commonly employed to modify the selectivity properties of the zeolite-based catalysts herein are oxides of phosphorus and magnesium. Thus, the catalysts herein can be treated with phosphorus and/or magnesium compounds in the manner described in U.S. Pat. Nos. 3,894,104; 4,049,573; 4,086,287; and 4,128,592, the disclosures of which are incorporated herein by reference.

Phosphorus, for example, can be incorporated into such catalysts at least in part in the form of phosphorus oxide in an amount of from about 0.25% to about 25% by weight of the catalyst composition, preferably from about 0.7% to about 15% by weight. Such incorporation can be readily effected by contacting the zeolite composite with a solution of an appropriate phosphorus compound, followed by drying and calcining to convert phosphorus in the zeolite to its oxide form. Preferred phosphorus-containing compounds include diphenyl phosphine chloride, trimethylphosphite and phosphorus trichloride, phosphoric acid, phenyl phosphine oxychloride, trimethylphosphate, diphenyl phosphinous acid, diphenyl phosphinic acid, diethylchlorothiophosphate, methyl acid phosphate and other alcohol-$P_2O_5$ reaction products. Particularly preferred are ammonium phosphates, including ammonium hydrogen phosphate, $(NH_4)_2HPO_4$, and ammonium dihydrogen phosphate, $NH_4H_2PO_4$. Calcination is generally conducted in the presence of oxygen at a temperature of at least about 150° C. However, higher temperatures, i.e., up to about 500° C. or higher are preferred. Such heating is generally carried out for 3–5 hours but may be extended to 24 hours or longer.

Magnesium oxide is another preferred difficultly reducible oxide which can be incorporated with the zeolite composites in a manner similar to that employed with phosphorus. Magnesium can comprise from about 0.25% to 25% by weight preferably from about 1% to 15% by weight present at least in part as magnesium oxide. As with phosphorus, magnesium oxide incorporation is effected by contacting the zeolite composite with an appropriate magnesium compound followed by drying and calcining to convert magnesium in the zeolite to its oxide form. Preferred magnesium-containing compounds include magnesium nitrate and magnesium acetate. Calcination times and temperatures are generally the same as recited hereinbefore for calcination of phosphorus-containing catalysts.

In addition to treatment of the zeolite composites to incorporate phosphorus and/or magnesium oxides as hereinbefore described in detail, such zeolites may also be modified in a substantially similar manner to incorporate thereon a variety of other oxide materials to enhance para-selectivity. Such oxide materials include oxides of boron (U.S. Pat. No. 4,067,920); antimony (U.S. Pat. No. 3,979,472); beryllium (U.S. Pat. No. 4,260,843); Group VIIA metals (U.S. Pat. No. 4,275,256); alkaline earth metals (U.S. Pat. No. 4,288,647); Group IB metals (U.S. Pat. No. 4,276,438); Group IVB metals (U.S. Pat. No. 4,278,827); Group VIA metals (U.S. Pat. No. 4,259,537); Group IA elements (U.S. Pat. No. 4,329,533); cadmium (U.S. Ser. No. 139,611, filed Apr. 11, 1980); iron and/or cobalt (U.S. Ser. No. 150,868, filed May 19, 1980); Group IIIB metals (U.S. Pat. No. 4,276,437); Group IVA metals (U.S. Pat. No. 4,302,620); Group VA metals (U.S. Pat. No. 4,302,621); and Group IIIA elements (U.S. Pat. No. 4,302,622).

Treatment of the zeolite catalysts to incorporate any of the foregoing oxide materials to enhance para-selectivity will generally occur before such catalysts are treated with water vapor in accordance with the present invention in order to provide enhanced aromatics conversion activity and/or even greater enhancement of the para-selective properties of such catalysts. Additional catalyst modifying procedures which may also optionally be employed to modify catalysts activity or selectivity include precoking and presteaming (i.e., before oxide incorporation), or combinations thereof.

In accordance with the present invention, the oxide-modified, para-selective, zeolite-based catalyst composites as hereinbefore described are treated with water vapor under particular conditions to enhance catalyst aromatics conversion activity and/or para-selectivity, i.e., to either restore diminished activity and/or diminished para-selectivity or improve inherent conversion activity and/or para-selectivity. Catalyst contact with water vapor occurs under conversion activity and/or para-selectivity enhancing conditions including a contact temperature of, e.g., from about 40° C. to 700° C., preferably from about 50° C. to 500° C., most preferably from about 50° C. to 150° C. Such conditions may also include a water vapor/catalyst contact time of from about 1 to 72 hours, preferably from about 2 to 24 hours.

The amount of water vapor employed is not critical so long as water vapor contact with the catalyst is sufficient to enhance the activity and/or para-selectivity of the treated catalyst with respect to its utility in promoting conversion of aromatics to dialkylsubstituted benzene compounds. Thus, generally catalyst can be contacted with at least about 0.005 gram of water vapor per gram of catalyst per hour, more preferably with at least about 0.01 gram of water vapor per gram of catalyst per hour.

Water vapor used to treat the specified catalysts of the present invention is admixed with an inert inorganic gaseous diluent. Inert diluent carriers of this type include air, nitrogen, carbon dioxide, helium and the like. During contact with the modified catalyst, the water vapor treating agent mixture should be maintained substantially free of organic diluents such as methanol. In a preferred method of treating the catalyst herein, air at ambient temperature (e.g., about 20° C. to 25° C.) is moistened with water and is then passed over the catalyst to be treated at the particular catalyst treatment temperatures recited above.

After water vapor treatment, the modified catalysts of the present invention may optionally again be calcined in conventional manner to render the catalyst suitable for use in promoting aromatics conversion reactions. Thus, after water vapor treatment is completed to the extent desired, the treated modified catalyst can be contacted with an atmosphere maintained at a temperature from about 100° C. to 1000° C. for a period of from about 1 to 72 hours. As with the water vapor treatment, calcination is generally conducted in a suitable atmosphere such as air, nitrogen, helium and the like.

It has been surprisingly discovered that treatment of the particular modified zeolite catalyst composites of this invention with water vapor in the manner herein described will provide catalysts having either enhanced activity and/or para-selectivity when such catalyst are used to promote the conversion of aromatic compounds to dialkyl substituted benzene compounds. Such enhancement occurs even with catalysts which are already active or already highly para-selective by virtue of having been modified by incorporating a difficultly reducible oxide of, for example, phosphorus, calcium and/or magnesium compounds. Alternatively, treatment of the zeolite catalysts herein in the particular manner of the present invention can permit elimination of the need for precoking procedures in order to reach given levels of para-selectivity, particularly after regeneration of such catalysts with air or other oxygen-containing gas.

The treated zeolite catalysts of the present invention are advantageously used to promote conversion of aromatic compounds to provide dialkyl-substituted benzene product mixtures which are highly enriched, in the para-dialkyl substituted benzene isomer. Conversion reactions of this type thus include aromatics alkylation, transalkylation and disproportionation.

Alkylation of aromatic compounds in the presence of the above-described cataylsts can be effected by contact of the aromatic with an alkylating agent. A particularly preferred embodiment involves the alkylation of toluene wherein the alkylating agents employed comprise methanol or other well known methylating agents or ethylene. The reaction is carried out at a temperature of between about 250° C. and about 750° C., preferably between about 300° C. and 650° C. At higher temperatures, the zeolites of high silica/alumina ratio are preferred. For example, ZSM-5 having a $SiO_2/Al_2O_3$ ratio of 30 and upwards is exceptionally stable at high temperatures. The reaction generally takes place at atmospheric pressure, but pressures within the approximate range of $10^5 N/m^2$ to $10^7 N/m^2$ (1–100 atmospheres) may be employed.

Some non-limiting examples of suitable alkylating agents would include olefins such as, for example, ethylene, propylene, butene, decene and dodecene, as well as formaldehyde, alkyl halides and alcohols, the alkyl portion thereof having from 1 to 16 carbon atoms. Numerous other aliphatic compounds having at least one reactive alkyl radical may be utilized as alkylating agents.

Aromatic compounds which may be selectively alkylated as described herein would include any alkylatable aromatic hydrocarbon such as, for example, benzene, ethylbenzene, toluene, dimethylbenzene, diethylbenzene, methylethylbenzene, propylbenzene, isopropylbenzene, isoproplymethylbenzene, or substantially any mono- or di-substituted benzenes which are alkylatable in the 4-position of the aromatic ring.

The molar ratio of alkylating agent to aromatic compound is generally between about 0.05 and about 5. For instance, when methanol is employed as the methylating agent and toluene is the aromatic, a suitable molar ratio of methanol to toluene has been found to be approximately 0.1 to 1.0 mole of methanol per mole of toluene. When ethylene is employed as the alkylating agent and toluene is the aromatic, a suitable molar ratio of ethylene to toluene is approximately 0.05 to 2.5 moles of ethylene per mole of toluene.

Alkylation is suitably accomplished utilizing a feed weight hourly space velocity (WHSV) of between about 1 and about 1000, and preferably between about 1 and about 200. The reaction product, consisting predominantly of the 1,4-dialkyl isomer, e.g. 1,4-dimethylbenzene, 1-ethyl-4-methylbenzene, etc., or a mixture of the 1,4- and 1,3-isomers together with comparatively smaller amounts of 1,2-dialkylbenzene isomer, may be separated by any suitable means. Such means may include, for example, passing the reaction product stream through a water condenser and subsequently passing the organic phase through a column in which chromatographic separation of the aromatic isomers is accomplished. Alkylation using the water vapor-treated catalysts of the present invention can provide product mixtures containing at least 80% or even 90% or more by weight of the para-dialkylbenzene isomer.

When transalkylation is to be accomplished, transalkylating agents are alkyl or polyalkyl aromatic hydrocarbons wherein alkyl may be composed of from 1 to about 5 carbon atoms, such as, for example, toluene, xylene, trimethylbenzene, triethylbenzene, dimethylethylbenzene, ethylbenzene, diethylbenzene, ethyltoluene, and so forth.

Another process embodiment of this invention relates to the selective disproportionation of alkylated aromatic compounds to produce dialkylbenzenes wherein the yield of 1,4-dialkyl isomer is in excess of the normal equilibrium concentration. In this context, it should be noted that disproportionation is a special case of transalkylation in which the alkylatable hydrocarbon and the transalkylating agent are the same compound, for example when toluene serves as the donor and acceptor of a transferred methyl group to produce benzene and xylene.

The transalkylation and disproportionation reactions are carried out by contacting the reactants with the above described treated modified zeolite catalyst at a temperature of between about 250° C. and 750° C. at a pressure of between atmospheric ($10^5 N/m^2$) and about 100 atmospheres ($10^7 N/m^2$). The reactant feed WHSV will normally fall within the range of about 0.1 to about 50. Preferred alkylated aromatic compounds suitable for utilization in the disproportionation embodiment comprise toluene, ethylbenzene, propylbenzene or substantially any mono-substituted alkylbenzene. These aromatic compounds are selectively converted to, respectively, 1,4-dimethylbenzene, 1,4-diethylbenzene, 1,4-dipropylbenzene, or other 1,4-dialkylbenzene, as appropriate, with benzene being a primary side product in each instance. The product is recovered from the reactor effluent by conventional means, such as distillation, to remove the desired products of benzene and dialkylbenzene, and any unreacted aromatic component is recycled for further reaction.

The aromatic conversion processes described herein may be carried out as batch type, semi-continuous or continuous operations utilizing a fixed or moving bed catalyst system. The catalyst after use in a moving bed reactor can be conducted to a regeneration zone wherein coke is burned from the catalyst in an oxygen-containing atmosphere, e.g. air, at an elevated temperature, after which the regenerated catalyst can be recycled to the conversion zone for further contact with the charge stock. In a fixed bed reactor, regeneration can be carried out in a conventional manner where an inert gas containing a small amount of oxygen (0.5–2%) is used to burn the coke in a controlled manner so as to limit the temperature to a maximum of around 500°–550° C.

The following examples will serve to illustrate certain specific embodiments of the hereindisclosed invention. These examples should not, however, be construed as limiting the scope of the invention, as there are many variations which may be made thereon without departing from the spirit of the disclosed invention, as those of skill in the art will recognize.

EXAMPLE I

A typical Mg and P-modified base catalyst composition illustrating the type of catalyst used in evaluating the various catalyst treating agents and procedures employed in this invention is described as follows. To prepare such a cataylst, NH$_4$ZSM-5 zeolite (9.75 kg.) having a crystal size of about 2 microns in the form of 1/16 inch diameter extrudate with a 35 weight percent alumina binder is used. The catalyst is presteamed at 593° C. for 2 hours at a gaseous steam rate of 2.83 l./min. The catalyst material is the impregnated with a solution of 3.9 kg. of diammonium acid phosphate in 16.2 l. of water and dried for about 16 hours in an open dish. The catalyst is then calcined in air at 500° C. for 3 hours to give a phosphorus modified zeolite. The resulting product is cooled, and a portion (1.36 kg.) is impregnated with a solution of 3.4 kg. of magnesium acetate tetrahydrate in 2.7 l. of water, dried and calcined in air at 500° C. for 1 hour. The final catalyst contains 7.1 weight percent magnesium, present at least in part as the oxide, and 2.67 weight percent phosphorus, present at least in part as the oxide.

EXAMPLE II

An Mg-P-ZSM-5 catalyst of the type described in Example I is used to promote ethylation of toluene. Using a reaction temperature of 425° C., a pressure of 100 psig, and a WHSV of 29.8 for toluene, 1.15 for ethylene, and 0.25 for hydrogen, a series of toluene ethylation reactions is conducted with the catalyst being subjected to water vapor treatment at various temperatures between each ethylation run. After each ethylation run, the catalyst sample is regenerated with air at 500° C. for 5 hours. Catalyst is then treated with a stream of air at 500 cc/min which is first moistened with water at ambient temperature and then passed into the catalyst bed maintained at the desired catalyst treatment temperature.

A description of the catalyst treating conditions and the toluene ethylation results achieved by using the various catalyst treating procedures are shown in Table I.

TABLE I

Ethylation of Toluene over Water-Vapor Treated Mg—P—ZSM-5

| Catalyst Treatment | Toluene Conversion % | Selectivity to Para-Ethyltoluene ( % p-Ethyltoluene / Ethyltoluenes ) |
|---|---|---|
| Fresh Catalyst | 9.7 | 94.4 |
| Water Vapor/Air Treatment at: | | |
| 500° C. | 9.8 | 93.9 |
| 400° C. | 9.3 | 94.9 |
| 200° C. | 9.3 | 94.1 |
| 110° C. | 9.5 | 95.1 |
| 90° C. | 8.7 | 96.0 |
| 50° C. | 9.9 | 96.6 |

The Table I data demonstrate that treatment of the Mg/P-modified ZSM-5 zeolite catalyst with water vapor in general either enhances the percent toluene conversion or enhances the para-selectivity properties of the catalyst for ethylation to toluene.

EXAMPLE III

A typical Ca- and P-modified base catalyst composition illustrating the type of catalyst used in evaluating the various catalyst treating agents and procedures employed in this invention is described as follows. To prepare such a cataylst, NH$_4$ZSM-5 zeolite (200 grams) having a crystal size of about 0.1 micron in the form of 1/16 inch diameter extrudate with a 35 weight percent alumina binder is used. If desired, the catalyst may be presteamed at 500° C. for 1 hour at a gaseous steam rate of 50 ml/min. The catalyst material is then impregnated with a solution of 80 grams of diammonium acid phosphate in 300 ml. of water, dried at 90° C. for about 2 hours in an open dish. The catalyst is then calcined in air at 500° C. for 2 hours to give a phosphorus modified zeolite, and the resulting product is cooled. A 6.0 portion of this PZSM-5 is impregnated with a solution of 6.0 grams of calcium acetate monohydrate in 15 ml. of water, dried at 80° C. for about 18 hours and calcined in air at 500° C. for 4 hours. The final catalyst contains 2.68 weight percent calcium, present as the oxide, and 2.80 weight percent phosphorus, present as the oxide.

EXAMPLE IV

A Ca-P-ZSM-5 catalyst of the type described in Example III is used to promote disproportionation and subsequently ethylation of toluene. Using a reaction temperature of 500° C. and a WHSV of 3.5 for toluene, toluene is disproportionated to give 12.8% conversion of toluene with a para-selectivity of xylene production of 63.0% p-xylene in xylenes. Thereafter the same catalyst is used to promote ethylation of toluene with ethylene at 400° C. with a WHSV=7/0.5 for toluene/ethylene. Such a reaction provides 18.6% toluene conversion and a para-selectivity of 86.4% p-ethyltoluene in ethyltoluene. The catalyst is then regenerated for 5 hours in air at 500° C.

The same Ca-P-ZSM-5 catalyst is then treated with a stream of air which is first moistened with water at ambient temperature and is then passed for 14 hours at the rate of 300 cc/minute into the catalyst bed maintained at 90° C. After calcination at 500° C. for 1 hour, disproportionation and ethylation of toluene are again carried out under the same conditions used with the untreated catalyst. Toluene disproportionation gives 12.6% toluene conversion with a para-selectivity of 66.3% p-xylene in xylenes. Toluene ethylation gives 19.1% conversion of toluene with a para-selectivity of 88.7% p-ethyltoluene in ethyltoluenes.

Such experimentation again demonstrates the enhancement in toluene conversion and/or catalyst para-selectivity which can be realized by catalyst water vapor treatment at 90° C.

EXAMPLE V

Another sample of Mg-P-ZSM-5 is prepared as follows: NH$_4$ZSM-5 zeolite (30 grams) having a crystal size of about 1 micron in the form of 1/16 inch diameter extrudate with 35 weight % alumina binder is impregnated with a solution of 15 g. of diammonium acid phosphate in 50 ml of water and at 50°–55° C. for 6 hours, dried at 80° C. for 16 hours then calcined in air at 500° C. for 2 hours to give 31.9 g. of P-ZSM-5. Analysis shows it contains 3.16% phosphorous, present at least in part as the oxide.

A 6.0 gram portion of this P-ZSM-5 is impregnated in a solution of 12 g of Mg(NO$_3$)$_2$.6H$_2$O in 8 ml of water at 90° C. for 2 hours, dried at 80° C. for 2 hours and calcined in air at 500° C. for 2 hours. The final Mg-P-ZSM- 5 zeolite contains 8.73% magnesium and 2.6% phosphorus.

EXAMPLE VI

The Mg-P-ZSM-5 of Example V is used to promote disproportionation of toluene and subsequently to promote ethylation of toluene. Disproportionation conditions include a temperature of 500° C. at a WHSV of 3.5 for toluene; ethylation conditions include a temperature of 400° C. and a WHSV of 7.5/0.5 for toluene/ethylene. After the ethylation run, catalyst is regenerated with air at 500° C. for 5 hours.

The catalyst is then treated with a stream of air which is first moistened with water at ambient temperature and is then passed into the catalyst bed maintained at the desired catalyst treatment temperature. Conditions of such catalyst treatments and results of toluene disproportionation and ethylation of toluene are set forth in Table II.

TABLE II

Toluene Disproportionation and Ethylation Over Water Vapor Treated Mg—P—ZSM-5

| | Disproportionation | Ethylation of Toluene |
|---|---|---|
| | % Tol. Conversion / % p-xylene / xylenes | % Tol. Conversion / % p-ethyltoluene / ethyltoluenes |
| Fresh Catalyst | 3.0/96 | 10.6/99+ |
| Water Vapor/ Air Treatment at: | | |
| 500° C. | 4.1/97 | 14.7/99+ |
| 50° C. | 4.0/97 | 16.5/99+ |

The Table II data again demonstrate that water vapor treatment of the catalyst in accordance with the present invention permits the catalyst to promote disproportionation and ethylation of toluene with enhanced toluene conversion and/or enhanced para-selectivity.

EXAMPLE VII

A magnesium modified ZSM-5 catalyst having a magnesium content of 6.8% and no phosphorus was used to promote ethylation of toluene substantially in accordance with the procedures set forth herein in Example II. Water vapor treatment increased the overall yield of para-ethyltoluene.

A description of the catalyst treating conditions and the toluene conversion results are shown in Table III.

TABLE III

Ethylation of Toluene over Water-Vapor Treated Mg—ZSM-5

| Catalyst Treatment | Toluene Conversion % | Selectivity to Ethyltoluenes % | Selectivity to Para-Ethyltoluene % p-Ethyltoluene Ethyltoluenes |
|---|---|---|---|
| Fresh Catalyst | 17.8 | 92.1 | 98.4 |
| Water Vapor/Air Treatment at: | | | |
| 500° C. | 18.2 | 93.5 | 98.6 |
| 400° C. | 18.9 | 93.5 | 98.5 |
| 300° C. | 19.1 | 93.9 | 98.3 |
| 200° C. | 18.4 | 93.7 | 98.4 |
| 115° C. | 18.6 | 94.3 | 98.6 |

What is claimed is:

1. A method for treating a chemically modified zeolite catalyst in order to enhance the aromatics conversion activity and/or the para-selectivity of said catalyst, said catalyst comprising both a crystalline zeolite material having a constraint index within the approximate range of 1 to 2 and a silica/alumina mole ratio of at least 12 and a minor proportion of one or more difficultly reducible oxides selected from the group consisting of oxides of the metals of Groups IA, IIA, IIIA, IVA, VA, VIA, VIIA, VIIIA, IB, IIIB, IVB and VB of the Periodic Chart and combination of phosphorus oxide with one or more of said metal oxides, said method comprising the steps of:

(i) contacting an inert inorganic gaseous diluent with liquid water, whereby said diluent becomes essentially saturated with water in the vapor state, and whereby water in the liquid state becomes dispersed in said diluent;

(ii) converting essentially all of said liquid water dispersed in said diluent to water in the vapor state by increasing the temperature of the water-containing diluent of step (i) to a temperature sufficient to accomplish such conversion; and (iii) contacting said catalyst with said essentially liquid water-free diluent of step (i) at a temperature between about 40° C. and 700° C. for a period of from about 1 to 72 hours and at a rate of at least about 0.005 gram of water per gram of catalyst per hour.

2. A method according to claim 1, whereby the increase in temperature achieved according to step (ii) is sufficient to at least double the vapor pressure of said water.

3. A method according to claim 1, wherein said inorganic diluent is selected from the group consisting of air, nitrogen, carbon dioxide, helium and mixtures thereof.

4. A method according to claim 3, wherein said contacting step (i) takes place at essentially ambient temperature, and wherein the temperature of said water-containing diluent of step (i) is increased to a temperature between about 40° C. and 700° C. in step (ii).

5. A method according to claim 4, wherein said steps (ii) and (iii) take place by maintaining said catalyst in a heated reactor and by passing said water-containing diluent of step (i) into said reactor.

6. A method according to claim 1, wherein said difficultly reducible oxide is selected from magnesium oxide, calcium oxide, combinations of magnesium oxide and phosphorus oxide and combinations of calcium oxide and phosphorus oxide.

7. A method according to claim 1, wherein the temperature of said water-containing diluent of step (i) is increased to a temperature from about 50° C. to 500° C. in step (ii).

8. A method according to claim 4, wherein said diluent is air.

9. A method according to claim 1, wherein said zeolite is selected from the group consisting of ZSM-5, ZSM-11, ZSM-12, ZSM-23, ZSM-35, ZSM-38 and ZSM-48.

10. A method according to claim 1, wherein said catalyst comprises only one difficultly reducible oxide, which is magnesium oxide, said catalyst not comprising phosphorus oxide.

11. A method for treating ZSM-5, said ZSM-5 comprising a minor proportion of one or more difficultly reducible oxides selected from the group consisting of oxides of the metals of Groups IA, IIA, IIIA, IVA, VA, VIA, VIIA, VIIIA, IB, IIIB, IVB and VB of the Periodic Chart and combinations of phosphorus oxide with one or more of said metal oxides, said method comprising the steps of:
  (i) moistening air with water at ambient temperature; and
  (ii) passing said water moistened air of step (i) into a reactor containing said ZSM-5, said reactor being maintained at a temperature between about 40° C. and 700° C., for a period of from about 1 to 72 hours and at a rate of at least about 0.005 gram of water per gram of catalyst per hour, whereby said ZSM-5 is contacted with water vapor.

12. A method according to claim 11, wherein said catalyst comprises only one difficultly reducible oxide, which is magnsium oxide, said catalyst not comprising phosphorus oxide.

* * * * *

UNITED STATES PATENT AND TRADEMARK OFFICE
CERTIFICATE OF CORRECTION

PATENT NO. : 4,548,914
DATED : Oct. 22, 1985
INVENTOR(S) : Chin-Chiun Chu

It is certified that error appears in the above-identified patent and that said Letters Patent is hereby corrected as shown below:

Col. 2, line 7, "hAve" should be --have--.

Col. 2, line 62, "difficulty" should be --difficultly--.

Col. 4, line 18, "decription" should be --description--.

Col. 9, line 1, "difficulty" should be --difficultly--.

Col. 10, line 65, "catalyst" should be --catalysts--.

Col. 13, line 12, "the" (second occurrence) should be --then--.

Col. 16, line 2, Claim 1, "1 to 2" should be --1 to 12--.

Col. 18, line 6, Claim 12, "magnsium" should be --magnesium--.

Signed and Sealed this

First Day of April 1986

[SEAL]

Attest:

DONALD J. QUIGG

Attesting Officer

Commissioner of Patents and Trademarks